United States Patent [19]

Shikata

[11] Patent Number: 5,105,813
[45] Date of Patent: Apr. 21, 1992

[54] ULTRASONIC DIAGNOSING APPARATUS WITH STEERABLE ULTRASONIC BEAMS

[75] Inventor: Hiroyuki Shikata, Ootawara, Japan

[73] Assignee: Kabushiki Kaisha Toshiba, Kawasaki, Japan

[21] Appl. No.: 571,441

[22] Filed: Aug. 23, 1990

[30] Foreign Application Priority Data

Aug. 25, 1989 [JP] Japan .................. 1-219401

[51] Int. Cl.⁵ ................................................ A61B 8/00
[52] U.S. Cl. ........................... 128/660.07; 128/661.09; 128/660.05
[58] Field of Search ............ 128/660.07, 660.04, 128/661.01, 661.08, 661.09, 661.10, 660.05, 661.01; 73/625, 626

[56] References Cited

U.S. PATENT DOCUMENTS

| | | | |
|---|---|---|---|
| 4,344,327 | 8/1982 | Yoshikawa et al. | 73/626 |
| 4,409,982 | 10/1983 | Plesset et al. | 128/661.01 |
| 4,462,092 | 7/1984 | Kawabuchi et al. | 73/626 |
| 4,470,308 | 9/1984 | Hayakawa et al. | 128/661.01 |
| 4,582,065 | 4/1986 | Adams | 128/662.03 |
| 4,605,009 | 8/1986 | Pourcelot et al. | 128/662.06 |
| 4,641,660 | 2/1987 | Bele | 128/661.01 |
| 4,690,150 | 9/1987 | Mayo, Jr. | 128/660.04 |
| 4,759,372 | 7/1988 | Umemura et al. | 128/661.01 |
| 4,817,433 | 4/1989 | Sato | 128/660.04 |
| 4,821,574 | 4/1989 | Takamizawa | 128/661.01 |
| 4,827,942 | 5/1989 | Lipschutz | 128/661.08 |
| 4,917,097 | 4/1990 | Proudian et al. | 128/661.01 |
| 4,937,797 | 6/1990 | Snyder et al. | 128/661.08 |

Primary Examiner—Francis Jaworski
Assistant Examiner—George Manuel
Attorney, Agent, or Firm—Cushman, Darby & Cushman

[57] ABSTRACT

A convex probe with N ultrasonic transducers placed in a row of predetermined curvature. Each of transducers is connected, via an array of switches, to an ultrasonic transmission/reception driver. Each of the driver forces a transducer to transmit or to receive ultrasonic beams. In addition, the drivers generate electrical signals corresponding to ultrasonic beams received at the transducers. All electrical signals from the drivers are added, and then manipulated to generate sets of data, which in turn are collected to produce a one-frame image to be displayed.

18 Claims, 6 Drawing Sheets

FIG. 6A STARTING OF STEERING SCAN MODE
FIG. 6B SETTING OF STEERING ANGLE
FIG. 6C CALCULATION OF DELAY VALUE
FIG. 6D READOUT OF DELAY VALUE
FIG. 6E SWITCHING OF TRANSMISSION/RECEPTION CHANNELS
FIG. 6F TRANSMISSION
FIG. 6G RECEPTION
FIG. 6H WRITING OF DATA IN FRAME MEMORY

ULTRASONIC DIAGNOSING APPARATUS WITH STEERABLE ULTRASONIC BEAMS

BACKGROUND OF THE INVENTION

1. Field of the Invention

The present invention relates to an ultrasonic diagnosing apparatus for performing convex scanning with respect to an object to be examined, e.g., a living body, by using a convex probe constituted by a large number of ultrasonic transducers arranged at a predetermined curvature so as to obtain ultrasonic data such as an M-mode image (motion image), a B-mode image (Tomography), a D-mode image (blood flow speed image), and a DF-mode image (CFM image: Color Flow Mapping image), and displaying a corresponding image for diagnosis.

2. Description of the Related Art

An ultrasonic diagnosing apparatus of this type is used to image and diagnose a circulatory organ such as a heart or a blood flow. In such a diagnosis, a doctor or the like obtains a B-mode image so as to obtain anatomical data of a heart to be diagnosed, or obtains an M-mode image so as to obtain function data of the heart. In addition, a D-mode or DF-mode image is obtained to check the behavior of blood flowing in the heart.

In diagnosis, B- and D-mode images are often obtained and observed simultaneously, thus effectively obtaining a diagnosis result of the heart. D-mode is performed by using the Doppler effect. In this case, a blood flow (blood cells) is processed as a moving object. Therefore, the angle defined by a blood flow direction and a ultrasonic beam must not be a right angle.

Since blood flows along a body surface, a linear scan scheme in which an ultrasonic beam is transmitted/received in a direction perpendicular to the body surface is not suitable for D-mode display. In contrast to this, a sector scan scheme in which an ultrasonic beam is transmitted/received in a direction which is not perpendicular to the body surface, i.e., in an oblique direction is suitable for D-mode display.

In the sector scan scheme, a B-mode display image has a sector shape, and the field of vision near the probe is very small. For this reason, image observation in the sector scan scheme is not easy to perform in comparison with other scan schemes such as the linear scan scheme and the convex scan scheme in which B-mode images have rectangular and convex shapes.

In the convex scan scheme in which image observation can be especially properly performed, no problem is posed in B-mode display. However, when D-mode data or DF-mode data is to be obtained, the following problems are posed.

A convex scanning operation for generating a B-mode image will be described below. As shown in FIG. 1, a convex probe 10 constituted by a large number of ultrasonic transducers 10a arranged at a predetermined curvature radius R is connected to an ultrasonic diagnosing apparatus main body (not shown) capable of electronic linear scanning. The convex probe 10 is in contact with a body surface 100a of an object 100 to be examined. Combinations of transducers to be simultaneously driven in the convex probe 10 are sequentially changed from one end to the other end of the probe 10. However, a beam deflection angle θ in each driving operation is constant. Therefore, the respective ultrasonic rasters in an ultrasonic transmission/reception wave region 102 are formed as if they are radiated in the radial direction of the probe 10.

On the other hand, as shown in FIG. 1, a blood vessel 104 extends substantially parallel to the body surface 100a of the object 100. Therefore, when the behavior of blood flowing in the blood vessel 104 is to be imaged and diagnosed by obtaining D-mode data or DF-mode data, since an ultrasonic beam at the central position of the probe 10 is perpendicular to the blood vessel 104, no Doppler signal is obtained. Hence, no D-mode or DF-mode data can be obtained. In contrast to this, ultrasonic beams 108 at both end positions of the probe 10 are not perpendicular to the blood vessel 104, and hence Doppler signals can be obtained. However, since the ultrasonic beams 108 are incident in opposite directions, opposite blood flow directions are displayed, and accurate diagnosis cannot be performed.

SUMMARY OF THE INVENTION

It is an object of the present invention to provide an ultrasonic diagnosing apparatus which facilitates image observation even in a convex scan scheme and allows a high-precision diagnosis of a circulatory organ by using blood flow data and tomographic images.

In order to achieve the above object, according to the present invention, there is provided an ultrasonic diagnosing apparatus comprising:
a convex probe constituted by N ultrasonic transducers arranged in a row at a predetermined curvature;
ultrasonic transmission/reception means for transmitting/receiving an ultrasonic beam to be transmitted/received from/by the convex probe while sequentially moving the ultrasonic beam on the convex probe in a direction in which the ultrasonic transducers are arranged;
signal processing/display means for performing signal processing of an ultrasonic reception signal obtained by the ultrasonic transmission/reception means so as to obtain predetermined image data, and displaying a corresponding image; and
control means for supplying the ultrasonic transmission/reception means with delay values for setting a transmission/reception direction of the ultrasonic beam to be parallel to a desirably set ultrasonic beam direction.

In addition, in order to achieve the above object, according to the present invention, there is provided an ultrasonic diagnosing apparatus comprising:
a convex probe constituted by N ultrasonic transducers arranged in a row at a predetermined curvature;
k (N>k) ultrasonic transmission/reception drive means each of which is driven to perform a transmitting or receiving operation with a delay corresponding to an externally supplied delay value;
switching means, inserted between the k ultrasonic transmission/reception drive mean and the N ultrasonic transducers of the convex probe, for switching and selecting k adjacent ultrasonic transducers to be driven by the k ultrasonic transmission/reception drive means so as to perform transmitting/receiving operations;
adding means for adding ultrasonic reception signals respectively obtained by the k ultrasonic transmission/reception drive means;
signal processing means for performing signal processing of the addition signal obtained by the adding means so as to calculate ultrasonic data;

display means for collecting a plurality of ultrasonic data calculated by the signal processing means so as to generate a one-frame image, and displaying the image; and control means for respectively supplying delay values for setting transmission/reception directions of ultrasonic beams to be parallel to a desirably set ultrasonic beam direction to the k ultrasonic transducers selected by the switching operation by the switching means.

Furthermore, in order to achieve the above object, according to the present invention, there is provided an ultrasonic diagnosing apparatus comprising:

a convex probe constituted by N ultrasonic transducers arranged in a row at a predetermined curvature;

k (N>k) ultrasonic transmission/reception drive means each of which is driven to perform a transmitting or receiving operation with a delay corresponding to an externally supplied delay value;

switching means, inserted between the k ultrasonic transmission/reception drive means and the N ultrasonic transducers of the convex probe, for switching and selecting k adjacent ultrasonic transducers to be driven by the k ultrasonic transmission/reception drive means so as to perform transmitting/receiving operations;

adding means for adding ultrasonic reception signals respectively obtained by the k ultrasonic transmission/reception drive means;

signal processing means for performing signal processing of the addition signal obtained by the adding means so as to calculate ultrasonic data;

display means for collecting a plurality of ultrasonic data calculated by the signal processing means so as to generate a one-frame image, and displaying the image; and control means for selectively executing first and second control modes, the first control mode being executed to supply a predetermined delay value pattern to the k ultrasonic transmission/reception drive means, and the second control mode being executed to respectively supply delay values for setting transmission/reception directions of ultrasonic beams to be parallel to a desirably set ultrasonic beam direction to the k ultrasonic transducers selected by the switching operation by the switching means.

With such an arrangement, convex scanning can be performed with respect to even a blood vessel extending substantially parallel to the body surface of an object to be examined in such a manner that each ultrasonic raster becomes parallel to an ultrasonic beam direction which is not perpendicular to the blood vessel. That is, each ultrasonic raster constituting each ultrasonic beam can be radiated on the blood vessel in the same incident direction. Therefore, the behavior of blood flowing in the vessel can be imaged and diagnosed by using D-mode data or DF-mode data based on a proper detection of blood flow directions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIGS. 6A to 6I show timings for executing convex scanning (steering scanning) according to the embodiment, in which FIG. 6A is a timing chart showing ON and OFF timings of a steering scan mode, FIG. 6B is a timing chart showing ON and OFF timings of data processing for setting a steering angle, FIG. 6C is a timing chart showing ON and OFF timings of calculation of delay values, FIG. 6D is a timing chart showing ON and OFF timings of a read operation of delay values, FIG. 6E is a timing chart showing ON and OFF timings of switching between transmission/reception channels, FIG. 6F is a timing chart showing ON and OFF timings of ultrasonic transmission, FIG. 6G is a timing chart showing ON and OFF timings of ultrasonic reception, FIG. 6H is a timing chart showing ON and OFF timings of a data write operation with respect to a frame memory (DSC), and FIG. 6I is a schematic view showing a shift of an ultrasonic raster to another raster.

DETAILED DESCRIPTION OF THE PREFERRED EMBODIMENTS

An ultrasonic diagnosing apparatus according to an embodiment of the present invention will be described below with reference to FIG. 2.

Figure 1:
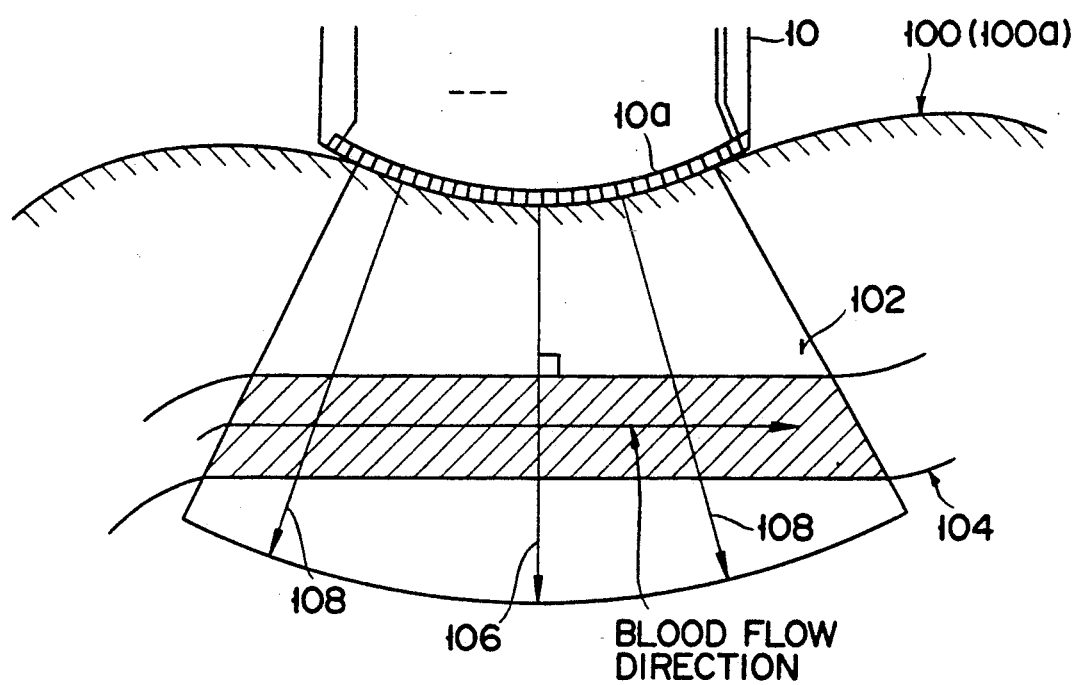
FIG. 1 is a view showing a conventional convex probe and convex scanning.
Figure 2:
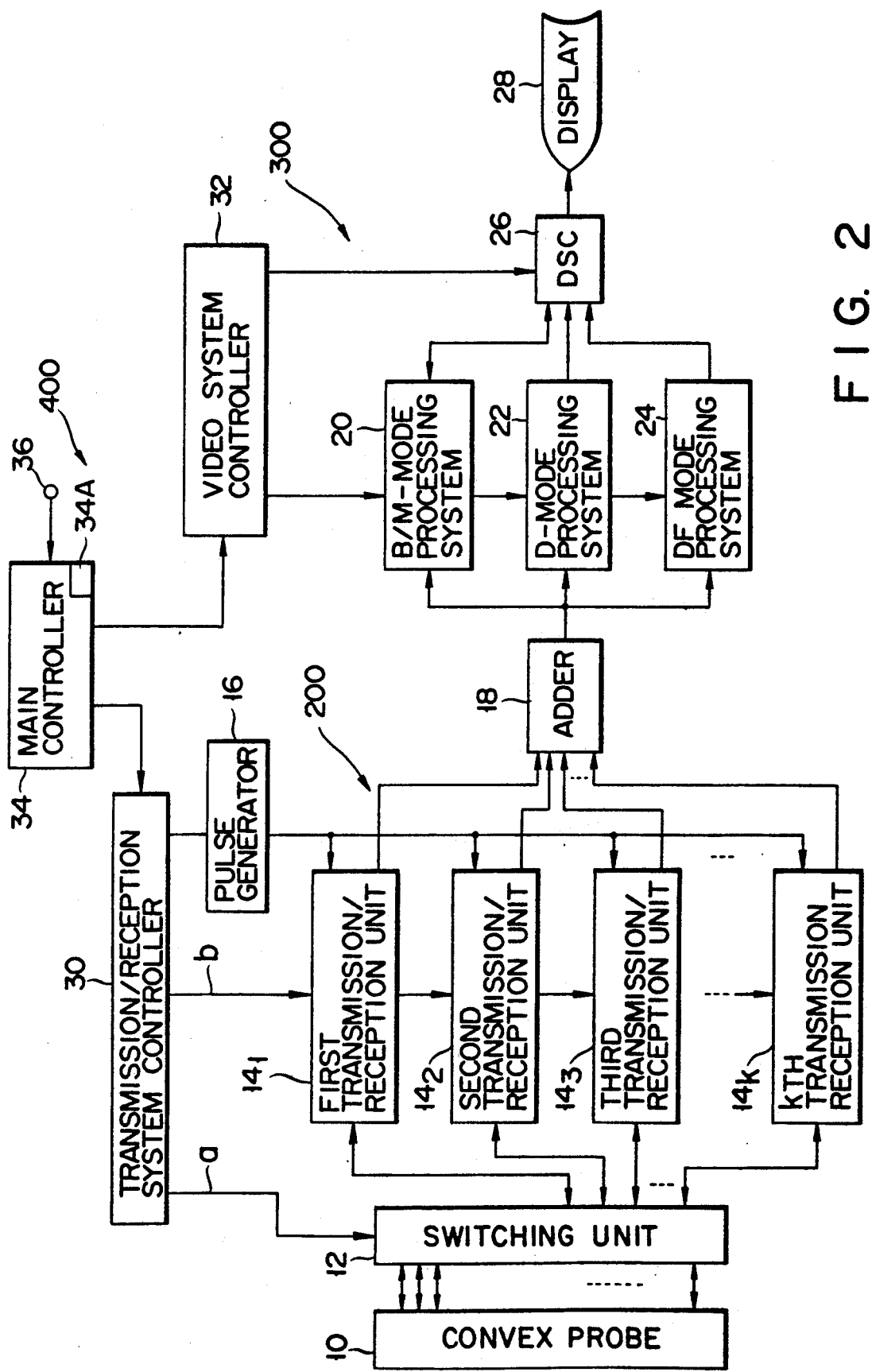
FIG. 2 is a block diagram showing an arrangement of an ultrasonic diagnosing apparatus capable of performing electronic convex scanning (steering scanning) according to a embodiment of the present invention.

Referring to FIG. 2, the ultrasonic diagnosing apparatus of this embodiment includes a convex probe 10 constituted by N small strip-like ultrasonic transducers arranged in the form of a sector at a curvature radius R. The convex probe 10 is to be brought into contact with a patient's body surface (not shown). The ultrasonic diagnosing apparatus of this embodiment further includes: an ultrasonic transmission/reception system 200 for driving the convex probe 10 to transmit/receive signals; a signal processing/display system 300 for performing signal processing of signals received from the ultrasonic transmission/reception system 200 so as to obtain ultrasonic image data, and displaying a corresponding image; and a control system 400 for controlling the ultrasonic transmission/reception system 200 and the signal processing/display system 300.

The ultrasonic transmission/reception system 200 is constituted by a switching unit 12 for switching/selecting combinations of k transducers (to be simultaneously driven) of the N ultrasonic transducers, k transmission/reception units 14 ($14_1, 14_2, 14_3, \ldots, 14_k$), a pulse generator 16 for generating rate pulses for determining drive timings in transmitting/receiving operations and an adder 18 for adding reception signals obtained by the k transmission/reception units $14_1, 14_2, 14_3, \ldots, 14_k$.

In this case, the switching unit 12 is designed to switch combinations of k transducers (to be simultaneously driven) of the N ultrasonic transducers of the convex probe 10 in response to a transducers switch signal a from a transmission/reception system controller 30 of the control system 400.

Each transmission/reception unit 14 comprises a transmitting section mainly constituted by a transmission delay unit and a pulser, and a receiving section mainly constituted by a preamplifier and a reception delay unit. The transmission and reception delay units respectively determine transmission and reception timings so as to set a deflection angle and a focal depth in response to delay signals b (transmission and reception delay signals) from the transmission/reception system controller 30 of the control system 400.

The signal processing/dis system 300 includes a B/M-mode processing system 20, a D-mode processing system 22, a DF-mode processing system 24, a DSC (digital scan converter) 26, having a frame memory 6A, for converting ultrasonic scan data into standard TV scan data, and a display 28.

The B/M-mode processing system 20 serves to detect a B-mode image by performing envelope detection of an addition echo signal from the adder 18 or to detect an M-mode image.

The D-mode processing system 22 phase-detects addition echo data obtained by ultrasonic transmission/reception of the Doppler mode, obtains a Doppler signal at a desired sampling point from the detection output, and obtains a blood flow speed image or data by performing frequency analysis of the Doppler signal using, e.g., a fast Fourier transform (FFT) method.

The DF-mode processing system 24, in a correlation scheme for example, checks the correlation between a plurality of reception wave signals obtained by performing ultrasonic scanning with respect to the same portion of an object to be examined a plurality of times, and obtains a blood flow profile (e.g., a blood flow direction, an average flow speed, a flow speed dispersion degree, and power in a blood flow direction) as CFM data represented by luminance, hue, and color tone levels.

The DSC 26 stores ultrasonic outputs from the B/M-mode processing system 20, the D-mode processing system 22, and the DF-mode processing system 24 in the frame memory 26A in units of ultrasonic rasters so as to form ultrasonic images in units of frames, and converts them into data for the standard TV scan scheme.

The display 28 converts an output from the DSC 26 into an analog signal and displays a corresponding image by, e.g., the standard TV scan scheme.

In this case, a video system controller 32 supplies control signals to the B/M-mode processing system 20, the D-mode processing system 22, and the DF-mode processing system 24, and also supplies data write/read control signals to the DSC 26.

The control system 400 comprises the transmission/reception system controller 30, the video system controller 32, a main control scan 34 including a scan table 34A, and a steering scan mode setting unit 36. The main controller 34 supplies control signals to the transmission/reception controller 30 and the video controller 32 in accordance with scan instructions from an operator.

In response to the control signal, the transmission/reception system controller 30 supplies a vibrator switch signal a to the switching unit 12 so as to switch combinations of k transducers (to be simultaneously driven) of the N ultrasonic transducers of the convex probe 10, and also supplies delay signals b (transmission and reception delay signals) to the transmission/reception units 14 ($14_1, 14_2, 14_3, \ldots, 14_k$) so as to determine transmission and reception timings for setting a deflection angle and a focal depth.

The video system controller 32 supplies control signals to the B/M-mode processing system 20, the D-mode processing system 22, and the DF-mode processing system 24, and also supplies a data write/read control signal to the DSC 26.

Figure 3:
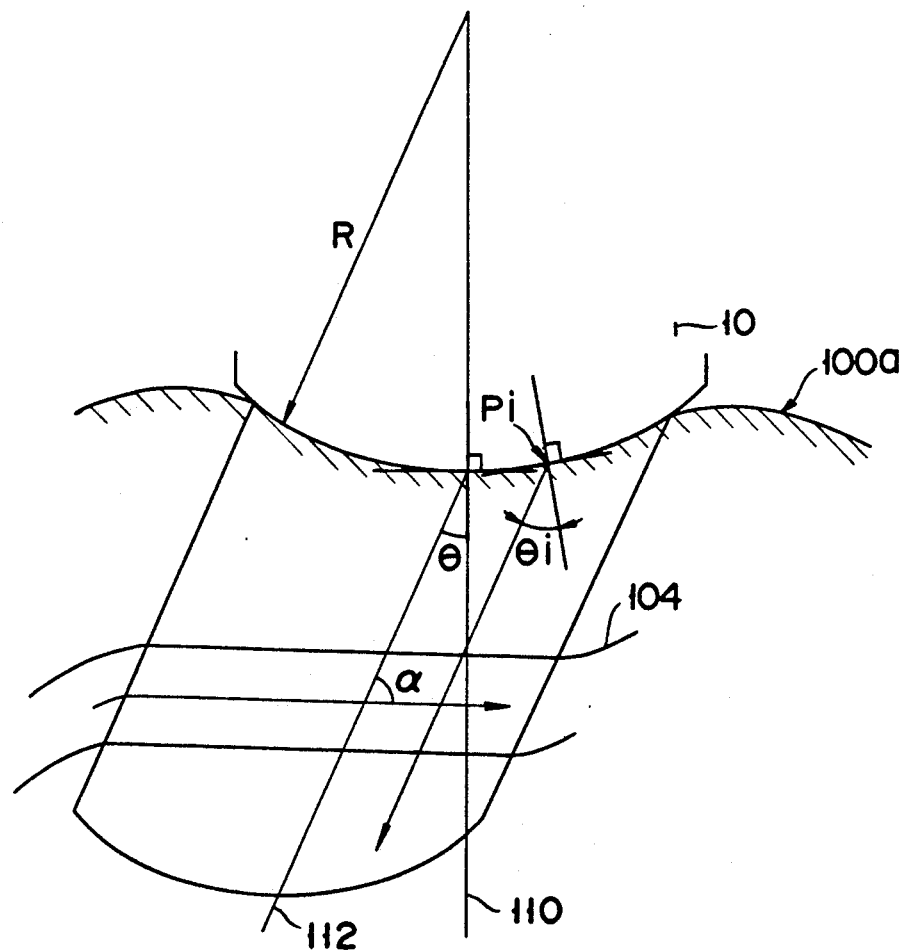
FIG. 3 is a view showing a relationship between the deflection angle and a propagation path of an ultrasonic beam in convex scanning (steering scanning) according to the embodiment.

The steering scan mode setting unit 36, as shown in FIG. 3 for example, outputs a line marker 110 from the central position of the convex probe 10 in, e.g., a vertical direction, and arbitrarily sets an angle $\theta$ of the line marker 110 in accordance with an operation of the operator so as to form a raster marker 112.

After the setting operation by means of the steering scan mode setting unit 34 is completed, the main controller 34 calculates a deflection angle $\theta i$ of an ultrasonic beam at a position Pi of a transducers group (selected to perform ultrasonic transmission/reception) on the basis of the curvature radius R, the position Pi, and the angle $\theta$ of the raster marker 112 so as to set a raster of the ultrasonic beam at the position Pi to be parallel to the raster marker 112. The main controller 34 then causes the transmission/reception system controller 30 to supply delay signals b (transmission and reception delay signals) corresponding to the deflection angle $\theta i$ to the transmission/reception units 14 ($14_1, 14_2, 14_3, \ldots, 14_k$).

According to the embodiment having the above-described embodiment, the angle $\theta$ of the raster marker 112 can be arbitrarily set by the operator, and an ultrasonic beam having the deflection angle $\theta i$ parallel to the angle $\theta$ can be transmitted and received at any position of the convex probe 10.

Even if a blood vessel 104 extends substantially parallel to a body surface 100a of an object 100 to be examined, and for example, the line marker 110 is perpendicular to the blood vessel 104, the angle defined by the raster marker 112 and the blood vessel 104 can be set to be a non-right angle $\alpha$, and convex scanning is performed such that the respective ultrasonic rasters are parallel to each other in the ultrasonic beam direction of the convex probe 10 regardless of its position.

That is, in convex scanning, each ultrasonic beam constituting each ultrasonic raster can be radiated onto the blood vessel 104 at a non-right angle in the same incident direction. Therefore, the behavior of blood in the blood vessel 104 can be imaged and diagnosed by using D-mode data and DF-mode data based on proper detection of a blood flow direction.

In this case, the above-described convex scanning in which a raster of an ultrasonic beam is parallel to the raster marker 112 is called a steering scan mode. This mode will be described in detail below with reference to FIGS. 3 to 6. According to the above description, in the steering scan mode, to perform scan control is to obtain the deflection angle $\theta i$ at which a raster of an ultrasonic beam becomes parallel to the raster marker 112. In practice, however, raster control is performed by obtaining a delay value corresponding to the deflection angle $\theta i$.

Figure 4:
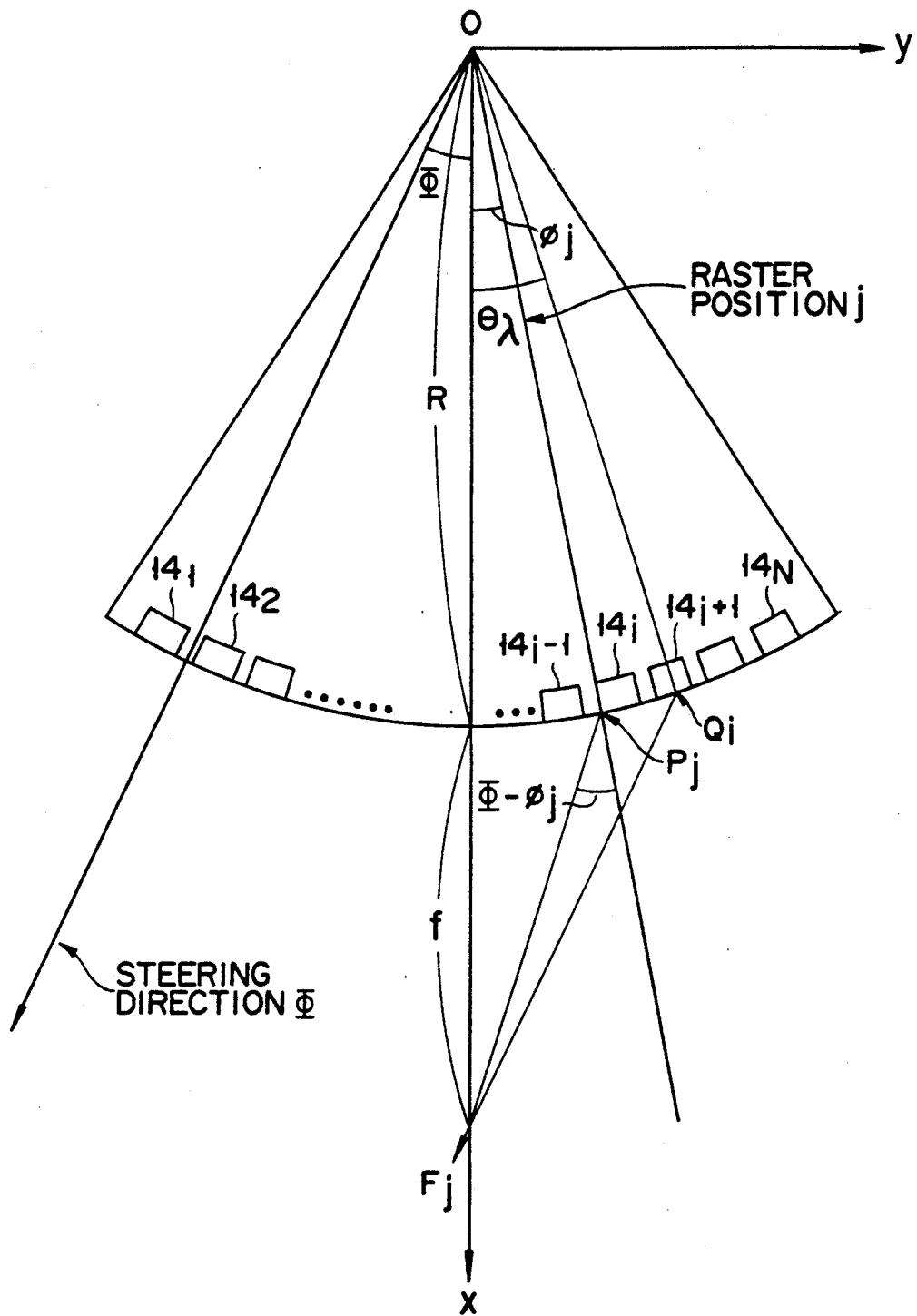
FIG. 4 is a view showing a method of calculating a deflection angle (steering angle) and delay values in convex scanning (steering scanning) according to the embodiment.

A method of calculating a delay value will be described below with reference to FIG. 4. In this case, a delay value with respect to an element (ultrasonic transducer) $14i$ is calculated on the basis of a steering angle $\Phi$, a raster position j, and a focus f. Assume that the angle of an ultrasonic beam at a raster position Pj with reference to the center of the curvature (curvature radius) R of the convex probe 10 is represented by $\theta j$. The raster position Pj is arbitrarily selected by the operator regardless of the arrangement of elements (ultrasonic transducers), and may be selected to be located right above each pixel. In addition, the raster position Pj may be selected such that-rasters are uniformly set on an image (equal raster intervals).

The coordinates of the raster position Pj are given as follows:

$$Pj = Pj(R \cos \phi j, R \sin \phi j)$$

Coordinates Fj(x,y) of the focal point are given as follows:

$$Fj(x,y) = Fj(R \cos \phi j + f \cos \Phi, R \sin \phi j + f \sin \Phi)$$

Coordinates Qi(x,y) of the element $14i$ are given as follows:

$$Qi(x,y) = Qi(R \cos \theta i, R \sin \theta i)$$

Therefore, a distance $\overline{Fj \cdot Qi}$ between the focal point and the element $14i$ can be obtained by:

$$Fj \cdot Qi = \sqrt{(R\cos\phi j + f\cos\Phi - R\cos\theta i)^2 + (R\sin\phi j + f\sin\Phi - R\sin\theta i)^2}$$

If the speed of sound is represented by v, a propagation time $(Fj \cdot Qi)/v$ of a sound wave between Fj and Qi can be given by:

$$(Fj \cdot Qi)/v = \left\{ \sqrt{(R\cos\phi j + f\cos\Phi - R\cos\theta i)^2 + (R\sin\phi j + f\sin\Phi - R\sin\theta i)^2} \right\}/v$$

In order to calculate a transmission delay value Dtji, Dtji is subtracted from a given constant value Ct as follows:

$$Dtji = Ct - \left\{ \sqrt{(R\cos\Phi j + f\cos\Phi - R\cos\theta i)^2 + (R\sin\phi j + f\sin\Phi - R\sin\theta i)^2} \right\}/v$$

In this case, Ct may be selected to be the minimum value for which Dtji becomes a positive value with respect to all the values of j and i.

A reception delay value Drji can be obtained with Cr being set as a constant value in the same manner as described above as follows:

$$Drji = (Fi \cdot Qi)/v - Cr$$

Figure 5:
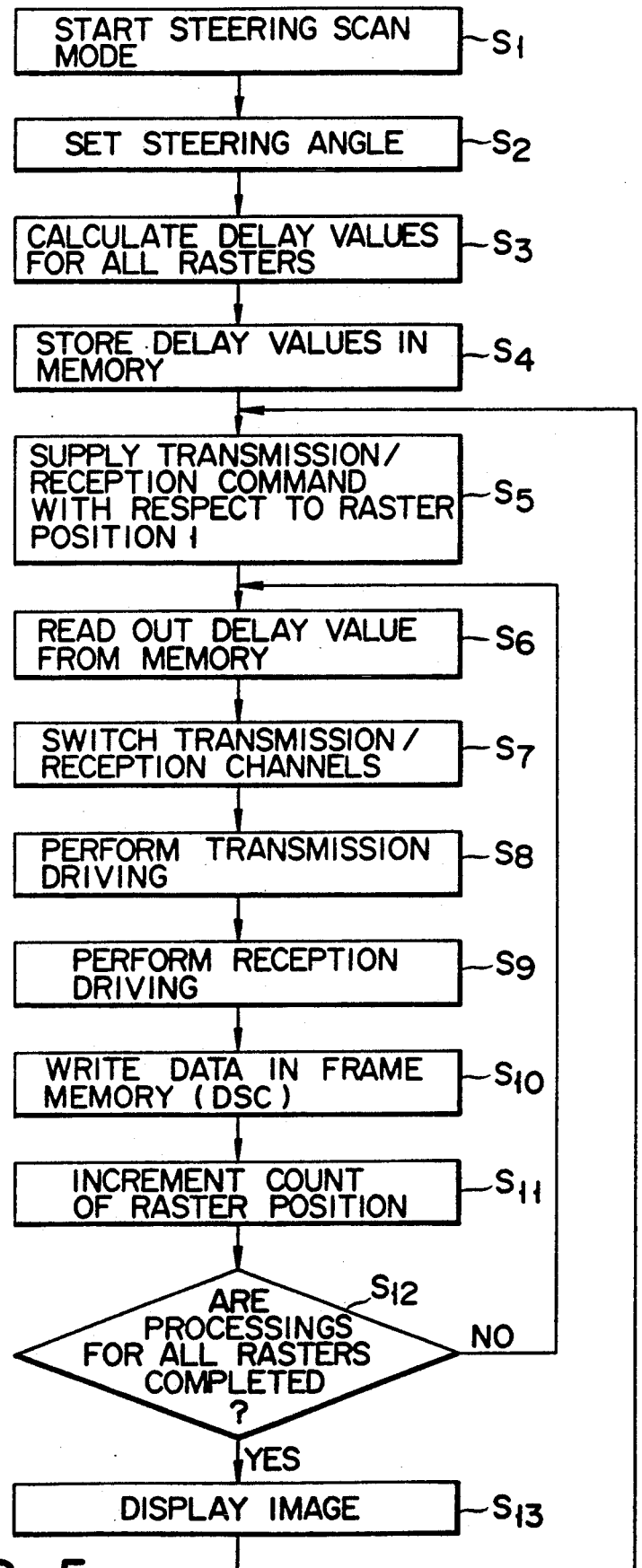
FIG. 5 is a flow chart showing a routine for executing convex scanning (steering scanning) according to the embodiment.

The above description is associated with the method of calculating delay values at a specific raster. The main controller 34 holds transmission/reception delay value calculation software which is programmed to execute this method. When a flow chart shown in FIG. 5 is executed, the software is started to calculate transmission and reception delay values for all the necessary rasters. The obtained values are temporarily stored in the memory 34A arranged in the main controller 34.

Figure 6I:
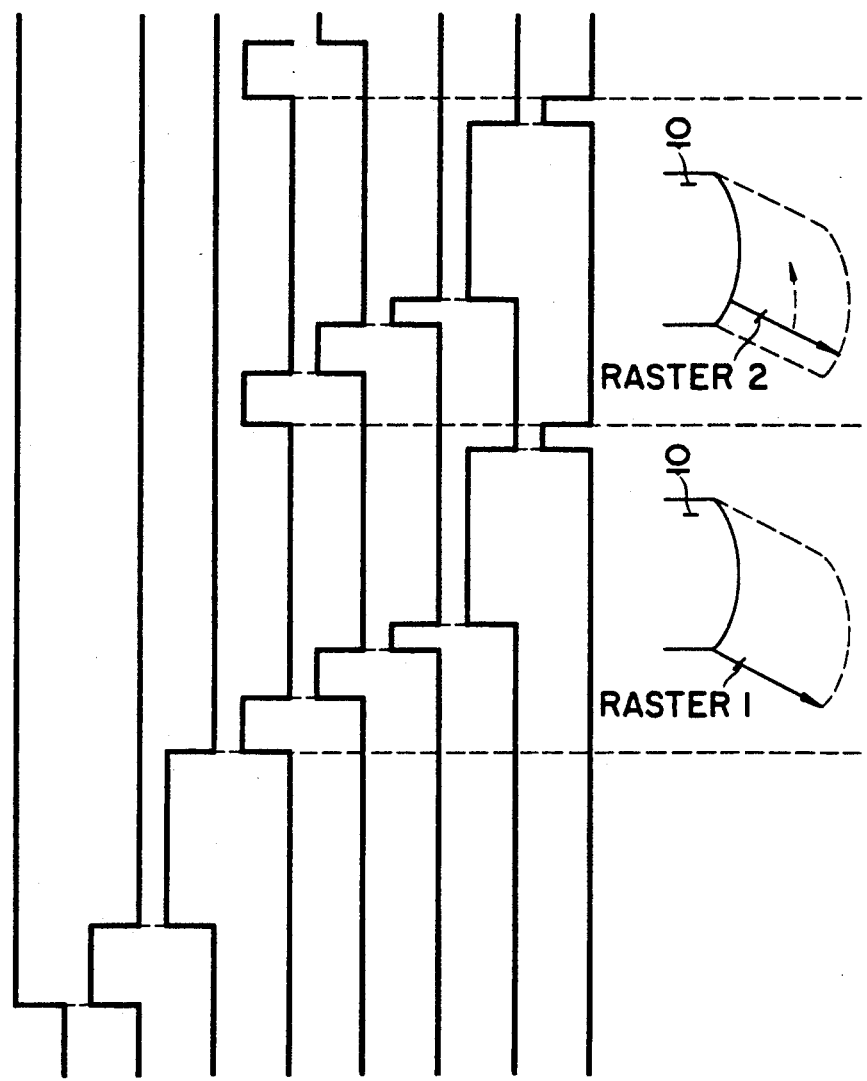

An operation sequence including the execution of the above-mentioned transmission/reception delay value calculation software will be described below with reference to FIGS. 5 and 6A to 6I. As shown in FIGS. 5 and 6A, the operator starts the steering scan mode setting unit 34 in step S1. In step S2, as shown in FIG. 6B, the operator operates the unit 34 so as to output the raster marker 112 on the display 28. The steering angle $\Phi$ is set by the display of the raster marker 112. In step S3, as shown in FIG. 6C, the main controller 34 executes the above-mentioned transmission/reception delay value calculation software in order to calculate transmission and reception delay values for all the necessary rasters. In step S4, the obtained values are temporarily stored in the memory 34A arranged in the main controller 34.

Subsequently, in step S5, the main controller 34 supplies a transmission/reception command associated with a raster 1 to the transmission/reception system controller 30. In this case, as shown in FIG. 6D, in step S6, a corresponding transmission/reception delay value is read out from the memory 34A and is supplied to the transmission/reception system controller 30. In step S7, as shown in FIG. 6E, the transmission/reception system controller 30 supplies a command for switching the transmission/reception channels to the switching unit 12. As shown in FIG. 6F, an ultrasonic transducer group is then switched to another group to perform transmitting/receiving operations (channel switching). In step S8, the corresponding ultrasonic transducer group is driven to perform a transmitting operation. In step S9, as shown in FIG. 6G, the group is driven to perform a receiving operation. In step S10, as shown in FIG. 6H, ultrasonic data obtained by the B/M-mode processing system 20, the D-mode processing system 22, and the DF-mode processing system 24 of the signal processing/display system 300 are written in the frame memory 26A of the DSC (digital scan converter) 26. That is, in steps S5 to S10, as shown in FIG. 6I, an image of the raster 1 is written in the frame memory 26A of the DSC 26. Subsequently, in step S11, the raster position is incremented. As a result, the processing in steps S5 to S10 is performed for a raster 2, and an image of the raster 2 is written in the frame memory 26A of the DSC 26, as shown in FIG. 6I. In step S12, it is checked whether the above-described processing is performed for all the rasters. If NO in step S12, the flow returns to step S5. If YES in step S12, a frame image formed in the frame memory 26A of the DSC 26 is displayed on the display 28.

It is apparent that the normal convex scan mode is restored by canceling the steering scan mode setting unit 34.

Various changes and modifications can be made within the spirit and scope of the invention.

As has been described above, according to the present invention, the apparatus includes the deflection angle setting means for setting the deflection angle of an ultrasonic beam at each position of a transducer group to perform ultrasonic transmission/reception on the basis of the curvature of the convex probe and the position of the transducer group so as to set each ultrasonic raster to be parallel to an ultrasonic beam direction which can be arbitrarily set. With this arrangement, convex scanning of even a blood vessel extending substantially parallel to a patient's body surface can be performed in such a manner that each ultrasonic raster is parallel to an ultrasonic beam direction which is not perpendicular to the blood vessel. That is, each ultrasonic beam constituting each ultrasonic raster can be radiated onto the blood vessel at a non-right angle in the same incident direction with respect to the blood vessel. Therefore, the behavior of blood in the blood vessel can be imaged and diagnosed by using D-mode data and DF-mode data based on proper detection of a blood flow direction.

According to the present invention, therefore, there is provided an ultrasonic diagnosing apparatus which facilitates observation and allows high-precision diagnosis of circulatory organs.

Additional advantages and modifications will readily occur to those skilled in the art. Therefore, the invention in its broader aspects is not limited to the specific details, and representative devices, shown and described. Accordingly, various modifications may be made without departing from the spirit or scope of the general inventive concept as defined by the appended claims and their equivalents.

What is claimed is:

1. An ultrasonic diagnosing apparatus comprising:
   a convex probe including a plurality of ultrasonic transducers arranged in a row at a predetermined curvature, each transducer being capable of performing a first function of transmitting and performing a second function of receiving ultrasonic beams;
   ultrasonic transmission/reception drive means for
      driving, in a predetermined sequence, each of said ultrasonic transducers to perform one of said two functions, and
      outputting electrical signals based on ultrasonic beams received at each of said ultrasonic transducers;
   signal processing/display means for processing said electrical signals outputted by said ultrasonic transmission/reception drive means in order to generate image data, and for displaying an image corresponding to the image data; and
   control means for
      adjustably selecting desired direction for transmitted/received ultrasonic beams at said ultrasonic transducers and
      supplying said ultrasonic transmission/reception drive means with groups of delay values, each group of values for setting the direction of transmitted/received ultrasonic beams at each of said transducers to be substantially parallel to said desired direction.

2. An apparatus as in claim 1, wherein said signal processing/display means includes a B-mode processing system for generating a tomographic image.

3. An apparatus as in claim 1, wherein said signal processing/display means includes a D-mode processing system for generating an image showing speed of flowing blood.

4. An apparatus as in claim 1, wherein said signal processing/display means includes a DF-mode processing system for generating a Color Flow Mapping image.

5. An apparatus as in claim 1, wherein said control means further comprises means for calculating said delay values to be supplied to said ultrasonic transmission/reception drive means.

6. An apparatus as in claim 1, wherein said control means further comprises means for calculating said delay values for setting the directions of said transmitted/received ultrasonic beams, each delay value being calculated partially based on four parameters, a curvature of said convex probe, a focal depth, a speed of sound, and a deflection angle of the ultrasonic beam corresponding to each delay value.

7. An ultrasonic diagnosing apparatus comprising:
   a convex probe including a plurality of ultrasonic transducers arranged in a row at a predetermined curvature, each transducer being capable of performing a first function of transmitting and performing a second function of receiving ultrasonic beams;
   a plurality of ultrasonic transmission/reception drive means, each ultrasonic transmission/reception drive means for
      driving one ultrasonic transducers to perform one of said two function, and
      outputting an electrical signal based on ultrasonic beams received at the driven ultrasonic transducer,
   the ultrasonic transmission/reception drive means being fewer than said ultrasonic transducers;
   switching means, disposed between said plurality of ultrasonic transmission/reception drive means and said plurality of ultrasonic transducers of said convex probe, for connecting each of said plurality of ultrasonic transmission/reception drive means to one of said ultrasonic transducers;
   means for adding amplitudes of said electrical signals outputted by said plurality of ultrasonic transmission/reception drive means and for outputting a signal having an amplitude equal to the result of the addition;
   means for processing the signal outputted by said adding means to produce a set of data;
   display means for collecting a plurality of set of data produced by said processing means to generate a one-frame image, and for displaying the image; and
   control means for
      adjustably selecting a desired direction for transmitted/received ultrasonic beams at said ultrasonic transducers and
      supplying each of said ultrasonic transmission/reception drive means with a group of delay values, each group of delay values for setting the direction of transmitted/received ultrasonic beams at each of said ultrasonic transducers to be parallel to said desired direction.

8. An apparatus as in claim 7, wherein said signal processing/display means includes a B-mode processing system for generating a tomographic image.

9. An apparatus as in claim 7, wherein said signal processing/display means includes a D-mode processing system for generating an image showing speed of flowing blood.

10. An apparatus as in claim 7, wherein said signal processing/display means includes a DF-mode processing system for generating a Color Flow Mapping image.

11. An apparatus as in claim 7, wherein said control means further comprises means for calculating said delay values to be supplied to said ultrasonic transmission/reception drive means.

12. An apparatus as in claim 7, wherein said control means further comprises means for calculating said delay values for setting the directions of said transmitted/received ultrasonic beams, each delay value being calculated partially based on four parameters, a curvature of said convex probe, a focal depth, a speed of sound, and a deflection angle of the ultrasonic beam corresponding to each delay value.

13. An ultrasonic diagnosing apparatus comprising:
a convex probe including a plurality of ultrasonic transducers arranged in a row at a predetermined curvature, each transducer being capable of performing a first function of transmitting and performing a second function of receiving ultrasonic beams;
a plurality of ultrasonic transmission/reception drive means, each ultrasonic transmission/reception drive means for
driving one of ultrasonic transducers to perform one of said two functions, and
outputting an electrical signal based on ultrasonic beams received at the driven ultrasonic transducer,
the ultrasonic transmission/reception drive means being fewer than said ultrasonic transducers;
switching means, disposed between said plurality of ultrasonic transmission/reception drive means and said plurality of ultrasonic transducers of said convex probe, for connecting each of said plurality of ultrasonic transmission/reception drive means to one of said ultrasonic transducers;
means for adding amplitudes of said electrical signals outputted by said plurality of ultrasonic transmission/reception drive means and for outputting a signal having an amplitude equal to the result of the addition;
means for processing the signal outputted by said adding means to produce a set of data;
display means for collecting a plurality of set of data produced by said processing means to generate a one-frame image, and for displaying the image; and
control means for selectively executing one of first and second control sequences, the first control sequence for supplying predetermined delay values to said plurality of ultrasonic/transmission reception drive means, and the second control sequence for
adjustably selecting a desired direction for transmitted/received ultrasonic beams at said ultrasonic transducers and
supplying each of said ultrasonic transmission/reception drive means with a group of computed delay values, each group of computed delay values for setting the direction of transmitted/received ultrasonic beams at each of said ultrasonic transducers to be parallel to said desired direction.

14. An apparatus as in claim 13, wherein said signal processing/display means includes a B-mode processing system for generating a tomographic image.

15. An apparatus as in claim 13, wherein said signal processing/display means includes a D-mode processing system for generating an image showing speed of flowing blood.

16. An apparatus as in claim 13, wherein said signal processing/display means includes a DF-mode processing system for generating a Color Flow Mapping image.

17. An apparatus as in claim 13, wherein said control means further comprises means for calculating said computed delay values to be supplied to said ultrasonic transmission/reception drive means.

18. An apparatus as in claim 13, wherein said controlling means further comprises means for calculating said computed delay values for setting the directions of said transmitted/received ultrasonic beams, each delay value being calculated partially based on four parameters, a curvature of said convex probe, a focal depth, a speed of sound, and a deflection angle of the ultrasonic beam corresponding to each delay value.

* * * * *